United States Patent [19]

Heffernan et al.

[11] Patent Number: 4,952,676

[45] Date of Patent: Aug. 28, 1990

[54] MONOCLONAL ANTIBODY-PLATINUM CO-ORDINATION COMPOUND COMPLEX

[75] Inventors: James G. Heffernan, Pangbourne; Michael J. Cleare, Reading, both of England; Donald H. Picker, Narbert, Pa.

[73] Assignee: Johnson Matthey PLC, London, England

[21] Appl. No.: 193,097

[22] Filed: Jul. 20, 1988

Related U.S. Application Data

[60] Division of Ser. No. 873,131, Jun. 11, 1986, Pat. No. 4,760,156, which is a continuation-in-part of Ser. No. 625,250, Jun. 27, 1984, abandoned.

[30] Foreign Application Priority Data

Jun. 11, 1985 [EP] European Pat. Off. ........ 85304130.9

[51] Int. Cl.$^5$ ...................... C07K 15/12; A61K 39/00
[52] U.S. Cl. .................................. 530/389; 530/390; 530/391; 530/388; 530/808; 424/85.9; 424/85.91; 514/885
[58] Field of Search ............................ 424/85.9, 85.91; 530/389–391, 808; 514/885

[56] References Cited

U.S. PATENT DOCUMENTS

| | | | |
|---|---|---|---|
| 4,115,418 | 9/1978 | Gale et al. | 260/429 R |
| 4,376,782 | 3/1981 | Turkevich et al. | 556/137 |
| 4,410,544 | 10/1983 | Berg et al. | 556/137 |
| 4,607,114 | 8/1986 | Nakayama et al. | 556/137 |
| 4,614,811 | 9/1986 | Gandolfi | 556/137 |
| 4,658,048 | 4/1987 | Totani et al. | 556/137 |
| 4,661,516 | 4/1987 | Brown et al. | 556/137 |
| 4,793,986 | 12/1988 | Serino et al. | 424/85.91 |

FOREIGN PATENT DOCUMENTS

| | | | |
|---|---|---|---|
| 0099133 | 1/1984 | European Pat. Off. | 424/85.91 |
| 2006776 | 10/1979 | United Kingdom . | |

OTHER PUBLICATIONS

Monoclonal Antibodies and Cancer Therapy, ed., Reisfeld et al., 1985, pp. 245–246 and 251–252.
Organometallic and Coordination Chemistry of Platinum, 1974, ed., Academic Press, Belluco.

*Primary Examiner*—Garnette Draper
*Attorney, Agent, or Firm*—Cushman, Darby & Cushman

[57] ABSTRACT

A platinum co-ordination compound linkable to a monoclonal antibody by a functional group which forms part of a moiety which stabilizes the antibody against in vivo hydrolysis. Also the use of such compounds in the treatment of cancer.

2 Claims, No Drawings

MONOCLONAL ANTIBODY-PLATINUM CO-ORDINATION COMPOUND COMPLEX

This is a division of application Ser. No. 873,131, filed June 11, 1986, now U.S. Pat. No. 4,760,156, which is continuation-in-part of application Ser. No. 625,250, filed June 27, 1984, now abandoned.

This invention relates to novel platinum co-ordination compounds for the treatment of cancer and which are also inter alia linkable to monoclonal antibodies. It also provides complexes comprising the novel platinum co-ordination complexes and nonoclonal antibodies, for use as site-specific or disease-specific chemotherapeutic agents.

The use of platinum co-ordination compounds, especially cisplatin (cis-diammine-dichloroplatinum II) and certain analogues thereof, in the chemotherapeutic treatment of cancer is now an established clinical technique, although efforts persist to find improved compounds. The problem with such compounds when administered as a composition together with an inert carrier or diluent is that they are absorbed generally into the systemic circulation from where they have a toxic effect on normal cells and tissues as well as on the diseased cells and tissues which they are designed to treat. In practice, the maximum dose that can be administered is limited not by pharmaceutical effectiveness but by toxicity, with the result that the patient suffers unpleasant or even severe side-effects.

In an attempt to render platinum compounds specific for certain types of tumour cell, European patent specification 0099133 proposes platinum complexed antitumour immunoglobulins prepared by reacting platinum salts, particularly $K_2PtCl_4$, with anti-tumour reactive immunoglobulins in for example phosphate buffered saline. The toxicity of the resulting complex is said to be lower than that of cisplatin. However, despite the presence of the immunoglobulin (which is an antibody produced from a tumour-associated antigen), the complexes are believed to be relatively non-specific in practical usage because of poorly defined metal stoichiometry and because they are hydrolysed in vivo before they reach the target tumour site, thereby losing their activity.

It has also been proposed in general pharmacological terms to link known chemotherapeutic agents to monoclonal antibodies for the purposes of rendering the agent site- or disease-sepecific but again the problem of in vivo stability remains.

It is an object of the present invention to provide co-ordination compounds of platinum which inter alia are chemically linkable to monoclonal antibodies in such a way that the desired in vivo stability is obtained. It is a further object of the invention to provide conjugate platinum co-ordination compound/monoclonal antibody complexes for localised pharmacological activity and which are stable in vivo until they reach the target site.

We have found that platinum co-ordination compounds can be linked to monoclonal antibodies in such a way that the desired in vivo stability is achieved by providing the compounds with a linkable functional group which forms part of an antibody-stabilising moiety.

Accordingly, the present invention provides a co-ordination compound of platinum linkable to a monoclonal antibody, wherein the compound includes an antibody-linkable functional group which forms part of an antibody-stabilising moiety.

Compounds according to the invention may be per se pharmacologically active as well as linkable to monoclonal antibodies.

Preferably the co-ordination compound of platinum has the general formula

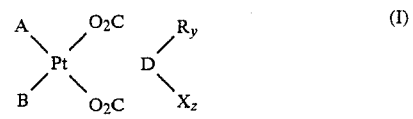

in which

A and B are the same or different selected from the class consisting of ammine and monodentate amine or A and B together comprise a bidentate amine, D is selected from the class consisting of substituted methylene and substituted dimethylene, R is selected from the class consisting of hydrogen, lower (for example up to four carbon atoms) alkyl, aryl, aralkyl, alkenyl, cycloalkyl, cycloalkenyl, alkoxy and hydroxy.

X is a funtionalised polymethylene moiety in which the functionalising group is selected from the class consisting of carboxylic acid, alcohol, thiol or amine, y is 1 if D is substituted methylene and is 1, 2 or 3 if D is substituted dimethylene and z is 1 if D is substituted methylene and is 1 or 2 if D is substituted dimethylene, with the proviso that where A and/or B is a monodentate cyclic alkylamine X may be a functionalising group selected from carboxylic acid, hydroxy, thio and amino.

The polymethylene chain X may optionally include ether, ester and/or peptide groups. Preferably the A and B groups are both cyclic alkylamine or both ammine.

Compounds according to the invention may exist as salts, for example as the potassium salt, or as solvated species.

The antibody-stabilising moiety in the above formula is the six- or seven-membered ring, depending on whether D is substituted methylene or substituted dimethylene as follows:

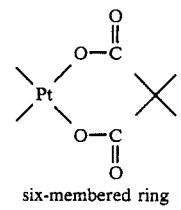

six-membered ring

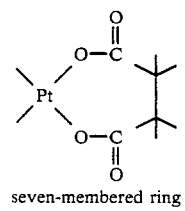

seven-membered ring

The invention also includes a conjugate platinum co-ordination compound/monoclonal antibody complex in which the monoclonal antibody is linked to the platinum compound via a functional group which forms part of an in vivo antibody-stabilising moiety.

Conjugate complexes according to the invention have the general formula

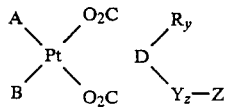

(II)

in which A, B, D, R, y and z have the same definition as in formula I, Y is a functionalised polymethylene moiety in which the functionalising group is selected from —CO$_2$—, —O—, —S— or —NH—, and Z is a monoclonal antibody.

The functionalised polymethylene moiety may optionally include ether, ester and/or peptide groups.

Preferably the —Y—Z moiety in the above formula II comprises or includes a peptide linkage although dioxide or disulphide bridge linkages are possible. In the formation of peptide-linked conjugate complexes, intermediate compounds comprising mixed anhydrides may be formed. Such intermediates have the general formula

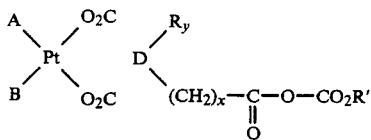

(III)

in which

A, B, D, R, and y have the same definition as in formula I, —(CH$_2$)$_x$— is a polymethylene moiety optionally including ether, ester and/or peptide groups, x is an integer (for example 1 to 15) and R' is selected from the class consisting of straight chain, branched chain and cyclic alkyl groups.

It is also an aspect of this invention to provide intermediates having general formula III as defined above.

Referring to the general formula (I) for the co-ordination compound of platinum, the polymethylene group of the functionalised polymethylene moiety X may have a total carbon chain length of C$_2$ to C$_{20}$, preferably C$_2$ to C$_{15}$, and may optionally include ether, ester and/or peptide groups. Examples of functionalised polymethylene moieties including ester groups are the short- and medium-chain polymethylene mono-esters of dibasic carboxylic acids such as succinnic acid; examples of the inclusion of ether groups are glycols.

Particular exemplary functionalised polymethylene moieties X optionally including ether and/or ester groups include the following:

—(CH$_2$)$_2$CO$_2$H
—(CH$_2$)$_4$CO$_2$H
—(CH$_2$)$_5$CO$_2$H
—(CH$_2$)$_6$OH
—(CH$_2$)$_{10}$CO$_2$H
—(CH$_2$)$_{11}$OH
—(CH$_2$)$_2$NH$_2$
—(CH$_2$CH$_2$O)$_3$H
—OCO(CH$_2$)$_2$CO$_2$H
—(CH$_2$)$_6$OCO(CH$_2$)$_2$CO$_2$H and
—(CH$_2$)$_{11}$OCO(CH$_2$)$_2$CO$_2$H Functionalised polymethylene moieties such as these are substituted for an acidic methylenic proton on a malonate or succinnate residue which forms, with platinum, an antibody-stabilising moiety comprising a six- or seven-membered ring. The other acidic methylenic proton (or protons) preferably remains (or remain) as such bu may be substituted with lower alkyl, aryl, aralkyl, alkenyl, cycloalkyl, cycloalkenyl, alkoxy or hydroxy, as represented by R in formula (I). Where R is other than hydrogen, we prefer that it is lower alkyl, for example methyl, ethyl or i-propyl.

The A and B groups are the same or different and are selected from amine and monodentate amine or together represent bidentate amine. By "monodentate amine" is meant either a straight chain, branched chain or cyclic alkylamine or an arylamine or aralkylamine. By "bidentate amine" is meant a diamine such as ethylene diamine or an alicyclic or aromatic analogue thereof such as 1,2-diaminocyclohexane or 1,2-diaminobenzene.

Accordingly, exemplary co-ordination compounds of platinum according to the invention include
[Pt((O$_2$C)$_2$C(C$_2$H$_5$)CO$_2$H)(c—C$_6$H$_{11}$NH$_2$)$_2$]
[Pt(O$_2$C)$_2$CH(CH$_2$)$_6$OH)(c—C$_6$H$_{11}$NH$_2$)$_2$]
[Pt((O$_2$C)$_2$CH(CH$_2$)$_4$CO$_2$H)(c—C$_6$H$_{11}$NH$_2$)$_2$]
[Pt((O$_2$C)$_2$C(C$_2$H$_5$)(CH$_2$)$_2$CO$_2$H)(c—C$_6$H$_{11}$NH$_2$)$_2$]
[Pt((O$_2$C)$_2$CH(CH$_2$)$_6$O$_2$C(CH$_2$)$_2$CO$_2$H)-(C—C$_6$H$_{11}$NH$_2$)$_2$]
[Pt((O$_2$C)$_2$CH(CH$_2$)$_{11}$OH)(c—C$_6$H$_{11}$NH$_2$)$_2$]
[Pt((O$_2$C)$_2$CH(CH$_2$)$_{11}$O$_2$C(CH$_2$)$_2$CO$_2$H)-(c—C$_6$H$_{11}$NH$_2$)$_2$]
[Pt((O$_2$C)$_2$CH(CH$_2$)$_7$CO$_2$H)(NH$_3$)$_2$]
[Pt((O$_2$C)$_2$CH(CH$_2$)$_5$CO$_2$H)(NH$_3$)$_2$]

The invention also includes a pharmaceutical composition for the treatment of cancer and comprising an effective amount of a compound of formula (I) or formula (II) in association with a pharmaceutically-acceptable carrier, diluent or excipient. Such compositions may be suitable for oral or parenteral administration, and may be in unit dosage form.

Compounds according to the invention may in general be prepared by reacting a platinum compound having the formula cis-[Pt(A)(B)I$_2$] with the appropriate functionalised malonate or succinnate. Compounds having the formula cis-[Pt(A)(B)I$_2$] are prepared by the method of S. C. Dhara, Indian Journal of Chemistry, volume 8, page 193 (1970), the contents of which are herein incorporated by reference. The reaction with malonate or succinnate comprises reacting the platinum compound with aqueous silver nitrate to form the diaquo complex to which is then added the malonate or succinnate. The resulting precipitate is filtered off, washed and dried.

The functionalised malonate or succinnate may be prepared by taking an appropriate halide compound of the functionalising group and protecting the functionalising group, reacting the protected compound with diethyl malonate, and hydrolysing to remove the protective group so forming the acid from the diethyl ester.

Examples of this reaction scheme are as follows:

(i) Br(CH$_2$)$_{11}$OH + HO$_2$CCH$_3$ → Br(CH$_2$)$_{11}$O$_2$CCH$_3$
(EtO$_2$C)$_2$CH$_2$ + Br(CH$_2$)$_{11}$O$_2$CCH$_3$ → (EtO$_2$C)$_2$CH(CH$_2$)$_{11}$O$_2$CCH$_3$
(EtO$_2$C)$_2$CH(CH$_2$)$_{11}$O$_2$CCH$_3$ + OH$^-$ → (HO$_2$C)$_2$CH(CH$_2$)$_{11}$OH
(ii) Br(CH$_2$)$_{10}$CO$_2$H + HOEt → Br(CH$_2$)$_{10}$CO$_2$Et

-continued

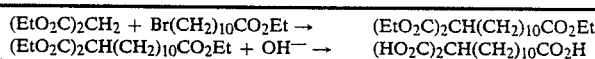

$(EtO_2C)_2CH(CH_2)_{10}CO_2Et + OH^- \rightarrow (HO_2C)_2CH(CH_2)_{10}CO_2H$

Where the functional group comprises an ester of a dibasic acid, the functionalised malonate may be prepared by refluxing tartronic acid with the dibasic acid anhydride in pyridine, for example

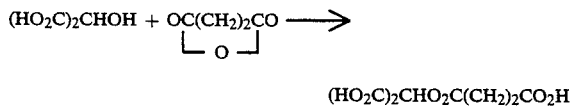

$\rightarrow (HO_2C)_2CHO_2C(CH_2)_2CO_2H$

Conjugate platinum coordination compound/monoclonal antibody complexes according to the invention may be prepared for example according to the following scheme, in which the functionalising group is $-CO_2H$:

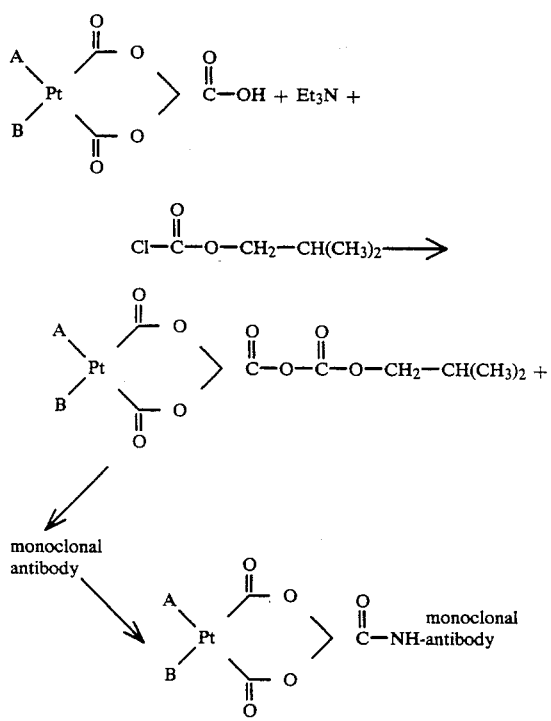

According to the above scheme, the antibody is linked to the platinum compound via a peptide group, and the six-membered ring system imparts in vivo stability to the complex so that it reaches the desired site without having been hydrolysed. Once at the desired site, enzymes which are present in tumour cells are able to catalyse hydrolysis thereby releasing the active anti-tumour moiety. Hence the stability imparted should be sufficient to enable the complex to reach the desired site unattacked but should not be so great that the complex is not susceptible to hydrolysis at the desired site.

The preparation various compounds according to the invention will now be described by way of example.

EXAMPLE 1

Preparation of
$[Pt\{(O_2C)_2CH(CH_2)_4CO_2H\}(c-C_6H_{11}NH_2)_2]$

Cis-$[PtI_2(c-C_6H_{11}NH_2)_2]$ was first prepared by the following method:

$K_2PtCl_4$(50 g, 0.12 mol) was dissolved in water (400 mls). Charcoal (2 g) was added and after stirring for two minutes the solution was filtered. An aqueous solution of KI (88.66 g, 0.528 mol) was added to the stirred filtrate. Cyclohexylamine (29.7 g, 0.3 mol) was added to the mixture which was stirred for a further 30 minutes at room temperature. The mixture was filtered and the precipitate was washed with water (3×150 ml), ethanol (2×150 ml) and diethylether (1×150 ml). The product was dried in air overnight at 50° C. Yield 73.7 g (94.1%).

The compound according to the invention was then prepared as follows:

$[PtI_2(c-C_6H_{11}NH_2)_2]$ (5 g, 0.0077 mol) was added to a stirred aqueous solution of $AgNO_3$ (2.6 g, 0.015 mol). The solution was heated with stirring at 50° C. for 3$h$ and filtered. A solution of $(HO_2C)_2CH(CH_2)_4CO_2H$ (1.88 g, 9.2 mmol) was partially neutralised with KOH (0.168 g, 3 mmol) and added to the filtrate above. The mixture was stirred overnight at room temperature and filtered to give a cream precipitate which was washed with water, ethanol and diethylether before being dried overnight. Yield (2.2 g, 48%).

| Elemental analysis | C | H | N |
|---|---|---|---|
| calculated(as monohydrate) | 39.15% | 6.24% | 4.56% |
| found | 40.39% | 5.93% | 5.44% |

EXAMPLE 2

Preparation of

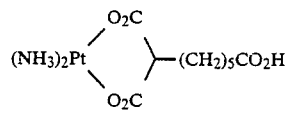

Cis-diammine-diiodo-platinum(II) (3.65 g, 7.6 mmol) was added as a solid to silver nitrate (2.52 g, 4.8 mmol) in water (30 ml) and stirred in the dark for 2½ hours. Silver iodide was filtered as a yellowish-brown solid. The sodium chloride test for silver ion was negative for the yellow filtrate. 2-Carboxyoctanedioic acid, (1.66 g, 7.6 mmol) was heated with sodium hydroxide (0.91 g, 22.9 mmol) dissolved in 30 ml water. The clear solution was brought to pH 6 with concentrated nitric acid. The 2-carboxyoctanedioic acid and cis-diammine-diaquo-platinum(II) solutions were combined with stirring at 50° C. for two hours. The clear pale yellow solution was acidified to pH 4 with concentrated nitric acid, affording a pale green precipitate. After standing 18 hours, the green product was washed with water, ethanol and ether and dried in vacuo (2.24 g, 72.2% yield).

The 2-carboxyoctanedioic malonate complex was recrystallized with a large volume of hot water, concentrated and chilled for 18 hours. A white solid was collected. Infrared (KBr) 3250 to 3100, 2930, 1700 to 1550 cm$^{-1}$.

EXAMPLE 3

Preparation of

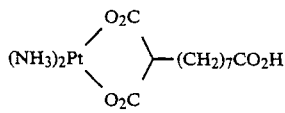

The method of Example 2 was followed, using the 2-carboxydecanedioic acid ligand (1.87 g, 7.6 mmol). The product was recrystallized from acetone/water to afford a white solid (2.14 g, 66.1%). Infrared (KBr) 3250 to 3090, 2920, 2850, 1760 to 1550 cm$^{-1}$.

| Elemental analysis | C | H | N |
|---|---|---|---|
| calculated | 27.90 | 4.69 | 5.92 |
| found | 27.45 | 4.54 | 5.88 |

The following compounds were also prepared by the method of either Example 1 or Example 2:

| COMPOUND | ANALYSIS | | |
|---|---|---|---|
| | C | H | N |
| [Pt{(O$_2$C)$_2$C(C$_2$H$_5$)CO$_2$H}(c-C$_6$H$_{11}$NH$_2$)] | | | |
| found % | 38.84 | 6.06 | 4.89 |
| (As H$_2$O adduct) calc. % | 39.15 | 6.24 | 4.56 |
| [Pt{(O$_2$C)$_2$CH(CH$_2$)$_4$CO$_2$H}(c-C$_6$H$_{11}$NH$_2$)$_2$] | | | |
| found % | 40.39 | 5.93 | 5.44 |
| (As H$_2$O adduct) calc. % | 39.15 | 6.24 | 4.56 |
| [Pt{(O$_2$C)$_2$CH(CH$_2$)$_6$OK}(c-C$_6$H$_{11}$NH$_2$)$_2$] | | | |
| found % | 38.57 | 6.69 | 4.78 |
| as monohydrate calc. % | 38.70 | 6.34 | 4.30 |
| [Pt{(O$_2$C)$_2$CH(CH$_2$)$_{11}$OK}(c-C$_6$H$_{11}$NH$_2$)$_2$] | | | |
| found % | 42.92 | 7.28 | 3.58 |
| as monohydrate calc. % | 43.26 | 7.12 | 3.88 |
| [Pt{(O$_2$C)$_2$CH(CH$_2$)$_{11}$O$_2$CCH$_2$CH$_2$CO$_2$H}(c-C$_6$H$_{11}$NH$_2$)$_2$] | | | |
| found % | 47.34 | 7.76 | 3.57 |
| calc. % | 47.05 | 7.11 | 3.66 |
| [Pt{(O$_2$C)$_2$CH(CH$_2$)$_7$CO$_2$H}(NH$_3$)$_2$] | | | |
| found % | 27.45 | 4.54 | 5.88 |
| calc. % | 27.90 | 4.69 | 5.92 |

EXAMPLE 4

Preparation of

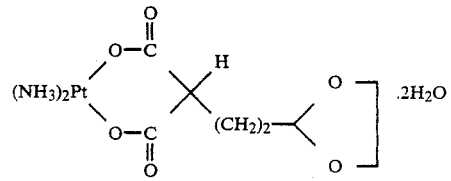

3.0 g of cis-[PtI$_2$(NH$_3$)$_2$] (6.2 mmol) was reacted with AgNO$_3$ (2.07 g, 12%) in water (40 ml) to form the diaquo species. This solution was added dropwise to a solution of 2-[2-(1,3-dioxolanyl)]ethyl propanedioic acid (1.3 g, 6.2 mmol). The pH of the reaction mixture was maintained at 6.05 using bicarbonate solution. The clear solution was heated to 60° C. for 2h and stirred at room temperature for 70h. The reaction mixture was evaporated to dryness and redissolved in a minimal volume of water. Chilling this solution yielded a white, crystalline solid, which was collected and washed with EtOH and Et$_2$O. Yield=0.91 g, 31% yield.

| Elemental analysis | C | H | N |
|---|---|---|---|
| calculated (.2H$_2$O) | 20.58 | 4.32 | 6.00 |
| found | 19.45 | 3.98 | 6.18 |

We claim:
1. A conjugate platinum co-ordination compound/monoclonal antibody complex having the general formula

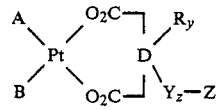

in which
A and B are the same or different selected from the class consisting of amine or monodentate amine or A and B together comprise a bidentate amine,
D is selected from the class consisting of substituted methylene or substituted dimethylene,
R is selected from the class consisting of hydrogen, lower alkyl, aryl, aralkyl, alkenyl, cycloalkyl, cycloalkenyl, alkoxy j or hydroxy,
y is 1 if D is substituted methylene or is 1 or 2 if D is substituted dimethylene,
z is 1 if D is substituted methylene or is 1 or 2 D is substituted dimethylene, and
Y is a functionalised polymethylene moiety in which the functionalising group is selected from the class consisting of —CO$_2$—, —O—, —S— or —NH—, and Z is a monoclonal antibody.
2. A conjugate complex according to claim 1 in which the functionalised polymethylene moiety comprises ether, ester and/or peptide groups.

* * * * *